US008309094B2

(12) United States Patent
Gerber et al.

(10) Patent No.: US 8,309,094 B2
(45) Date of Patent: Nov. 13, 2012

(54) ANTIBODY-DRUG CONJUGATES

(75) Inventors: Hans-Peter Gerber, Montclair, NJ (US); John Francis DiJoseph, Woodbridge, NJ (US); Kiran Manohar Khandke, Nanuet, NY (US); Kimberly Ann Marquette, Somerville, MA (US); Puja Sapra, River Edge, NJ (US); Lioudmila Gennadievna Tchistiakova, Andover, MA (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 13/435,731

(22) Filed: Mar. 30, 2012

(65) Prior Publication Data

US 2012/0251558 A1 Oct. 4, 2012

Related U.S. Application Data

(60) Provisional application No. 61/602,349, filed on Feb. 23, 2012, provisional application No. 61/593,549, filed on Feb. 1, 2012, provisional application No. 61/470,576, filed on Apr. 1, 2011.

(51) Int. Cl.
*A61K 39/395* (2006.01)
*A61K 39/44* (2006.01)
*C07K 16/30* (2006.01)

(52) U.S. Cl. ............... 424/178.1; 424/179.1; 424/133.1; 530/391.7; 530/387.3

(58) Field of Classification Search ......................... None
See application file for complete search history.

(56) References Cited

U.S. PATENT DOCUMENTS

| | | | |
|---|---|---|---|
| 5,869,053 A | 2/1999 | Stern et al. | |
| 6,884,869 B2 | 4/2005 | Senter et al. | |
| 7,098,308 B2 | 8/2006 | Senter et al. | |
| 7,256,257 B2 | 8/2007 | Doronina et al. | |
| 7,423,116 B2 | 9/2008 | Doronina et al. | |
| 7,498,298 B2 | 3/2009 | Doronina et al. | |
| 7,745,394 B2 | 6/2010 | Doronina et al. | |
| 7,750,116 B1* | 7/2010 | Doronina et al. | 530/330 |
| 8,044,778 B2* | 10/2011 | Monroe | 340/426.19 |
| 2006/0088522 A1* | 4/2006 | Boghaert et al. | 424/133.1 |
| 2007/0231333 A1* | 10/2007 | Boghaert et al. | 424/155.1 |
| 2009/0148942 A1 | 6/2009 | McDonagh et al. | |
| 2009/0226465 A1 | 9/2009 | Jackson | |
| 2010/0017382 A1* | 1/2010 | Katragadda et al. | 707/4 |
| 2010/0021483 A1* | 1/2010 | Boghaert et al. | 424/181.1 |
| 2012/0064600 A1* | 3/2012 | Boghaert et al. | 435/188 |

FOREIGN PATENT DOCUMENTS

| | | |
|---|---|---|
| WO | WO 2007/067602 A1 | 6/2007 |
| WO | WO 2007/106744 A2 | 9/2007 |
| WO | WO 2010/111659 | 9/2010 |

OTHER PUBLICATIONS

Chothia, C., et al., "Canonical Structures for the Hypervariable Regions of Immunoglobulins", J. Mol. Biol., 196(4):901-917 (1987).
Chothia, C., et al., "Conformations of Immunoglobulin Hypervariable Regions", Nature, 342:877-883 (1989).
Ducry, L., et al., "Antibody-Drug Conjugates: Linking Cytotoxic Payloads to Monoclonal Antibodies", Bioconjugate Chemistry, 21:5-13 (2010).
Fellouse, F.A., et al., "High-throughput Generation of Synthetic Antibodies from Highly Functional Minimalist Phage-displayed Libraries", J. Mol. Biol., 373(4):924-940 (2007).
Hamel, E., et al., "Interaction of Dolastatin 10 with Tubulin: Induction of Aggregation and Binding and Dissociation Reactions", Molecular Pharmacology, 47:965-976 (1995).
Hamel, E., et al., "Binding of Dolastatin 10 to Tublin at a Distinct Site for Peptide Antimitotic Agents Near the Exchangeable Nucleotide and Vinca Alkaloid Sites", The Journal of Biological Chemistry, 265(28):17141-17149 (1990).
Muller, J.F., et al., "Tubulin-Binding Drug Screening by MALDI-TOFMS", Anal. Chem., 78:4390-4397 (2006).
Jayasena, S.D., "Aptamers: An Emerging Class of Molecules That Rival Antibodies in Diagnostics", Clinical Chemistry, 45(9):1628-1650 (1999).
MacCallum, R.M., et al., "Antibody-antigen Interactions: Contact Analysis and Binding Site Topography", J. Mol. Biol., 262:732-745 (1996).
Makabe, K., et al., "Thermodynamic Consequences of Mutations in Vernier Zone Residues of a Humanized Anti-human Epidermal Growth Factor Receptor Murine Antibody, 528", Journal of Biological Chemistry, 283(2):1156-1166.
Simeoni, M., et al., "Predictive Pharmacokinetic-Pharmacodynamic Modeling of Tumor Growth Kinetics in Xenograft Models after Administration of Anticancer Agents", Cancer Research, 64:1094-1101 (2004).

* cited by examiner

*Primary Examiner* — Phuong Huynh
(74) *Attorney, Agent, or Firm* — Lynn D. Apelgren

(57) ABSTRACT

Disclosed are anti-5T4 antibody drug conjugates and methods for preparing and using the same.

6 Claims, No Drawings

ANTIBODY-DRUG CONJUGATES

This application claims priority from copending provisional application No. 61/602,349 filed Feb. 23, 2012, 61/593,549 filed Feb. 1, 2012 and 61/470,576 filed Apr. 1, 2011 the entire disclosure of which is hereby incorporated by reference.

FIELD

The present invention generally relates to anti-5T4 antibody-drug conjugates for the treatment of cancer.

BACKGROUND

Antibody-drug conjugates (ADCs) combine the binding specificity of monoclonal antibodies with the potency of chemotherapeutic agents. The technology associated with the development of monoclonal antibodies to tumor associated target molecules, the use of more effective cytotoxic agents, and the design of chemical linkers to covalently bind these components, has progressed rapidly in recent years (Ducry L., et al. Bioconjugate Chemistry, 21:5-13, 2010).

Promising ADCs such as SGN-75 (US2009/148942) and trastuzumab-DM1 (US2009/0226465) are currently in clinical trials. However, as other tumor associated antigens are considered for targets, numerous challenges remain. Each monoclonal antibody must be characterized separately, an appropriate linker designed, and a suitable cytotoxic agent identified that retains its potency upon delivery to tumor cells. One must consider the antigen density on the cancer target and whether normal tissues express the target antigen. Other considerations include whether the entire ADC is internalized upon binding the target; whether a cytostatic or cytotoxic drug is preferable when considering possible normal tissue exposure and/or the type and stage of the cancer being treated; and, whether the linker connecting the antibody to the drug payload is a cleavable or a non-cleavable linkage. Furthermore, the antibody to drug moiety conjugation ratio must be sufficient without compromising the binding activity of the antibody and/or the potency of the drug. It is evident that ADCs are complex biologics and the challenges to develop an effective ADC remain significant.

The human 5T4 tumor associated antigen is the target antigen of the present invention. It has recently been shown that the 5T4 antigen is expressed in high levels on certain highly tumorigenic cells, also called tumor-initiating cells (WO2010/111659). Tumor-initiating cells show resistance to standard therapies and are believed to be responsible for tumor recurrence and metastasis and therefore present yet another obstacle for ADC development.

The novel anti-5T4 ADCs of the present invention overcome the challenges associated with ADC technology and provide highly specific and potent ADCs that bind to tumor cells expressing the 5T4 antigen and deliver sufficient cytotoxic drug to the cells, thus providing an innovative and effective treatment for cancer.

SUMMARY

In one embodiment, an antibody-drug conjugate of the present invention has the formula: Ab-(LU-D)p or a pharmaceutically acceptable salt thereof wherein, Ab is an anti-5T4 antibody or antigen binding portion thereof, comprising a heavy chain variable region having a VH CDR1 region as shown in SEQ ID NO: 5, a VH CDR2 region as shown in SEQ ID NO: 6, and a VH CDR3 region as shown in SEQ ID NO: 7; LU is a linker unit selected from the group consisting of maleimidocaproyl and maleimidocaproyl-Val-Cit-PABA; p is an integer from about 1 to about 8; and D is a Drug unit selected from the group consisting of MMAE, MMAF, and MMAD.

The present invention further provides anti-5T4 antibody-drug conjugates wherein said anti-5T4 antibody or antigen binding portion thereof, comprises a heavy chain variable region having (a) a VH CDR1 region as shown in SEQ ID NO: 5, (b) a VH CDR2 region as shown in SEQ ID NO: 6, and (c) a VH CDR3 region as shown in SEQ ID NO: 7.

The present invention further provides an anti-5T4 antibody-drug conjugate wherein said anti-5T4 antibody or antigen binding portion thereof, comprises a light chain variable region having (a) a VL CDR1 region as shown in SEQ ID NO: 8, (b) a VL CDR2 region as shown in SEQ ID NO: 9, and (c) a VL CDR3 region as shown in SEQ ID NO: 10.

The present invention further provides an anti-5T4 antibody-drug conjugate wherein said anti-5T4 antibody or antigen binding portion thereof, further comprises a heavy chain variable region having (a) a VH CDR1 region as shown in SEQ ID NO: 5, (b) a VH CDR2 region as shown in SEQ ID NO: 6, and (c) a VH CDR3 region as shown in SEQ ID NO: 7 and a light chain variable region having (a) a VL CDR1 region as shown in SEQ ID NO: 8, (b) a VL CDR2 region as shown in SEQ ID NO: 9, and (c) a VL CDR3 region as shown in SEQ ID NO: 10.

The present invention further provides an anti-5T4 antibody-drug conjugate wherein said anti-5T4 antibody or antigen binding portion thereof, comprises the VH region of SEQ ID NO: 3 and the VL region of SEQ ID NO: 4.

The present invention further provides an anti-5T4 antibody-drug conjugate wherein said anti-5T4 antibody consists of a heavy chain having SEQ ID NO: 1 and a light chain having SEQ ID NO: 2.

The present invention further provides an anti-5T4 antibody-drug conjugate wherein:
(a) said anti-5T4 antibody consists of a heavy chain having SEQ ID NO:1 and a light chain having SEQ ID NO: 2, (b) said LU is maleimidocaproyl, (c) said Drug is MMAF, and (d) p is an integer of about 4.

The present invention further provides an anti-5T4 antibody-drug conjugate wherein:
(a) said anti-5T4 antibody consists of a heavy chain having SEQ ID NO:1 and a light chain having SEQ ID NO: 2, (b) said LU is maleimidocaproyl-Val-Cit-PABA, (c) said Drug is MMAE, and (d) p is an integer of about 4.

The present invention further provides an anti-5T4 antibody-drug conjugate wherein:
(a) said anti-5T4 antibody consists of a heavy chain having SEQ ID NO:1 and a light chain having SEQ ID NO: 2, (b) said LU is maleimidocaproyl-Val-Cit-PABA, (c) said Drug is MMAD, and (d) p is an integer from about 1 to about 8.

The present invention further provides an anti-5T4 antibody-drug conjugate wherein: (a) said anti-5T4 antibody consists of a heavy chain having SEQ ID NO:15 and a light chain having SEQ ID NO: 2, (b) said LU is maleimidocaproyl-Val-Cit-PABA, (c) said Drug is MMAE, and (d) p is an integer of about 1 to about 8.

The present invention provides an anti-5T4 antibody-drug conjugate wherein said antibody recognizes an epitope on human 5T4 antigen wherein said epitope comprises amino acid residues 173-258 and 282-361 of the amino acid sequence of SEQ ID NO: 11.

The present invention provides a pharmaceutical composition comprising an antibody-drug conjugate indicated above and a pharmaceutically acceptable carrier.

The present invention further provides a method of treating a 5T4-positive cancer in a patient in need thereof, comprising administering to said patient an antibody-drug conjugate indicated above.

The present invention further provides a method of treating a 5T4-positive cancer wherein said cancer is selected from the group consisting of carcinomas of the bladder, breast, cervix, colon, endometrium, kidney, lung, esophagus, ovary, prostate, pancreas, liver, skin, stomach, and testes.

More preferably, the present invention provides a method of treating a 5T4-positive cancer wherein said cancer is selected from the group consisting of colorectal, breast, pancreatic, and non-small cell lung carcinomas.

The invention further provides an antibody-drug conjugate indicated above for use in therapy.

The invention further provides the use of an antibody-drug conjugate indicated above for the manufacture of a medicament.

The invention further provides the use indicated above, wherein said use is for the treatment of a 5T4-positive cancer and wherein said cancer is selected from the group consisting of carcinomas of the bladder, breast, cervix, endometrium, kidney, lung, esophagus, ovary, prostate, pancreas, skin, stomach, and testes.

More preferably, the invention further provides the use indicated above, wherein said use is for the treatment of a 5T4-positive cancer wherein said cancer is selected from the group consisting of colorectal, breast, pancreatic, and non-small cell lung carcinomas.

The invention further provides a nucleic acid that encodes an anti-5T4 antibody, a vector comprising said nucleic acid, and a host cell comprising said vector.

The invention further provides a process for producing an anti-5T4 antibody comprising cultivating the host cell comprising the above mentioned vector and recovering the antibody from the cell culture.

The invention further provides a process for producing an anti-5T4 antibody-drug conjugate comprising: (a) taking the antibody recovered from the cell culture, (b) chemically linking said antibody via a linker unit selected from the group consisting of maleimidocaproyl or maleimidocaproyl-Val-Cit to a Drug unit selected from the group consisting of MMAE, MMAD, or MMAF, and (c) purifying the antibody-drug conjugate.

DETAILED DESCRIPTION

The present invention provides anti-5T4 antibody-drug conjugates for the treatment of cancer. In order that the present invention is more readily understood, certain terms are first defined.

All amino acid abbreviations used in this disclosure are those accepted by the United States Patent and Trademark Office as set forth in 37 C.F.R. §1,822 (B)(I).

5T4 refers to the 5T4 oncofetal antigen, a 72 kDa highly glycosylated transmenbrance glycoprotein comprising a 42 kDa non-glycosylated core (see U.S. Pat. No. 5,869,053). Human 5T4 is expressed in numerous cancer types, including carcinomas of the bladder, breast, cervix, colon, endometrium, kidney, lung, esophagus, ovary, prostate, pancreas, liver, skin, stomach, and testes. Highly tumorigenic cells, also called cancer stem cells or tumor-initiating cells have been shown to have high levels of 5T4 expression (WO2010/111659). Anti-5T4 antibodies of the invention include antibodies that specifically bind the human 5T4 antigen (see US 2007/0231333).

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also any antigen binding fragment (i.e., "antigen-binding portion") or single chain thereof, fusion proteins comprising an antibody, and any other modified configuration of the immunoglobulin molecule that comprises an antigen recognition site including, for example without limitation, Fab, Fab', F(ab')$_2$, an Fd fragment consisting of the VH and CH1 domains, an Fv fragment consisting of the VL and VH domains of a single arm of an antibody, an isolated complementarity determining region (CDR), scFv, single domain antibodies (e.g., shark and camelid antibodies), maxibodies, minibodies, intrabodies, diabodies, triabodies, tetrabodies, v-NAR and bis-scFv.

An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonincal class as the subject variable region (Chothia and Lesk, J Mol Biol 196(4): 901-917, 1987). When choosing FR to flank subject CDRs, e.g., when humanizing or optimizing an antibody, FRs from antibodies which contain CDR1 and CDR2 sequences in the same canonical class are preferred.

A "CDR" of a variable domain are amino acid residues within the variable region that are identified in accordance with the definitions of the Kabat, Chothia, the cumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington, D.C. The positions of the CDRs may also be identified as the structural loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

The term "monoclonal antibody" (Mab) refers to an antibody that is derived from a single copy or clone, including e.g., any eukaryotic, prokaryotic, or phage clone, and not the method by which it is produced. Preferably, a monoclonal antibody of the invention exists in a homogeneous or substantially homogeneous population.

"Humanized" antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50 (1999) and Fellouse, F. A., et al, J. Mol. Biol., 373(4):924-40 (2007)).

Tables 1 and 2 below depict preferred CDRs for the antibodies of the present invention.

TABLE 1

| Antibody | LCDR1 | LCDR2 | LCDR3 |
|---|---|---|---|
| A1 | KASQSVSNDVA SEQ ID NO: 8 | FATNRYT SEQ ID NO: 9 | QQDYSSPWT SEQ ID NO: 10 |
| A3 | KASQDVDTAVA SEQ ID NO: 17 | WASTRLT SEQ ID NO: 18 | QQYSSYPYT SEQ ID NO: 19 |

TABLE 2

| Antibody | HCDR1 | HCDR2 | HCDR3 |
|---|---|---|---|
| A1 | NFGMN SEQ ID NO: 5 | WINTNTGEPRYAEEFKG SEQ ID NO: 6 | DWDGAYFFDY SEQ ID NO: 7 |
| A1-IgG4 | GYTFTNFGMN SEQ ID NO: 14 | WINTNTGEPRYAEEFKG SEQ ID NO: 6 | DWDGAYFFDY SEQ ID NO: 7 |
| A3 | TYAMN SEQ ID NO: 22 | RIRSKSNNYATYYADSVKD SEQ ID NO: 23 | QWDYDVRAMNY SEQ ID NO: 24 |

The present invention includes an antibody or antigen binding portion thereof, that comprises:
a) a light chain variable region comprising:
i) a LCDR1 having an amino acid sequence selected from the group consisting of SEQ ID NOs: 8 and 17;
ii) a LCDR2 having an amino acid sequence selected from the group consisting of SEQ ID NOs: 9 and 18; and
iii) a LCDR3 having an amino acid sequence selected from the group consisting of SEQ ID NOs: 10 and 19; and
b) a heavy chain variable region comprising:
i) a HCDR1 having an amino acid sequence selected from the group consisting of SEQ ID NOs: 5 and 22;
ii) a HCDR2 having an amino acid sequence selected from the group consisting of SEQ ID NOs: 6 and 23; and
iii) a LCDR1 having an amino acid sequence selected from the group consisting of SEQ ID NOs: 7 and 24.

A preferred antibody or antigen binding portion thereof, of the invention comprises:
a) a LCVR comprising: a LCDR1 of SEQ ID NO: 8, a LCDR2 of SEQ ID NO: 9, and a LCDR3 of SEQ ID NO: 10; and
b) a HCVR comprising: a HCDR1 of SEQ ID NO: 5, a HCDR2 of SEQ ID NO: 6, and a HCDR3 of SEQ ID NO: 7.

Preferred monoclonal antibodies of the invention are referred to herein as A1 (a humanized anti-5T4 IgG1 antibody); A1-IgG4 (a humanized anti-5T4 IgG4 antibody); A3 (a mouse/human chimeric antibody); and A3hu (a humanized anti-5T4 IgG1 antibody). The SEQ ID NOs of the amino acid sequences encoding Mabs A1, A1-IgG4 and A3 are provided in Table 3 below:

TABLE 3

| Mab | LC | HC | LCVR | LCDR1 | LCDR2 | LCDR3 | HCVR | HCDR1 | HCDR2 | HCDR3 |
|---|---|---|---|---|---|---|---|---|---|---|
| A1 | 2 | 1 | 4 | 8 | 9 | 10 | 3 | 5 | 6 | 7 |
| A1-IgG4 | 2 | 12 | 4 | 8 | 9 | 10 | 13 | 5 | 6 | 7 |

TABLE 3-continued

| Mab | LC | HC | LCVR | LCDR1 | LCDR2 | LCDR3 | HCVR | HCDR1 | HCDR2 | HCDR3 |
|---|---|---|---|---|---|---|---|---|---|---|
| A3 | 2 | 15 | 21 | 22 | 23 | 24 | 16 | 17 | 18 | 19 |
| A3hu | 30 | 25 | 31 | 32 | 33 | 34 | 26 | 27 | 28 | 29 |

The phrases "an antibody recognizing an antigen" and "an antibody specific for an antigen" are used interchangeably herein with the term "an antibody which binds specifically to an antigen."

Anti-5T4 Antibody-Drug conjugate refers to an anti-5T4 antibody or antigen binding portion thereof, as described herein linked to a cytotoxic drug moiety (D) via a linker unit molecule (LU).

Linker Unit (LU): LU describes the direct or indirect linkage of the antibody to the drug. Attachment of a linker to a mAb can be accomplished in a variety of ways, such as through surface lysines, reductive-coupling to oxidized carbohydrates, and through cysteine residues liberated by reducing interchain disulfide linkages. A variety of ADC linkage systems are known in the art, including hydrazone-, disulfide- and peptide-based linkages.

Drug (D): A drug is any substance having biological or detectable activity, for example, therapeutic agents, detectable labels, binding agents, etc., and prodrugs, which are metabolized to an active agent in vivo. The terms drug and payload are used interchangeably. In some embodiments, the Drug is an auristatin, such as auristatin E (also known in the art as a derivative of dolastatin-10) or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include AFP, MMAF, and MMAE. The synthesis and structure of exemplary auristatins are described in U.S. Pat. Nos. 6,884,869, 7,098,308, 7,256,257, 7,423,116, 7,498,298 and 7,745,394, each of which is incorporated by reference herein in its entirety and for all purposes.

Auristatins have been shown to interfere with microtubule dynamics and nuclear and cellular division and have anticancer activity. Auristatins of the present invention bind tubulin and can exert a cytotoxic or cytostatic effect on a 5T4 expressing cell or cell line. There are a number of different assays, known in the art, that can be used for determining whether an auristatin or resultant antibody-drug conjugate exerts a cytostatic or cytotoxic effect on a desired cell or cell line. Methods for determining whether a compound binds tubulin are known in the art. See, for example, Muller et al., Anal. Chem 2006, 78, 4390-4397; Hamel et al., Molecular Pharmacology, 1995 47: 965-976; and Hamel et al., The Journal of Biological Chemistry, 1990 265:28, 17141-17149.

Examples of drugs or payloads are selected from the group consisting of DM1 (maytansine, N2'-deacetyl-N2'-(3-mercapto-1-oxopropyl)- or N2'-deacetyl-N2'-(3-mercapto-1-oxopropyl)-maytansine), mc-MMAD (6-maleimidocaproyl-monomethylauristatin-D or N-methyl-L-valyl-N-[(1S,2R)-2-methoxy-4-[(2S)-2-[(1R,2R)-1-methoxy-2-methyl-3-oxo-3-[[(1S)-2-phenyl-1-(2-thiazolyl)ethyl]amino]propyl]-1-pyrrolidinyl]-1-[(1S)-1-methylpropyl]-4-oxobutyl]-N-methyl-(9Cl)-L-valinamide), mc-MMAF (maleimidocaproyl-monomethylauristatin F or N-[6-(2,5-dihydro-2,5-dioxo-1H-pyrrol-1-yl)-1-oxohexyl]-N-methyl-L-valyl-L-valyl-(3R,4S,5S)-3-methoxy-5-methyl-4-(methylamino)heptanoyl-(αR,βR,2S)-β-methoxy-α-methyl-2-pyrrolidinepropanoyl-L-phenylalanine) and mc-Val-Cit-PABA-MMAE (6-maleimidocaproyl-ValcCit-(p-aminobenzyloxycarbonyl)-monomethylauristatin E or N-[[[4-[[N-[6-(2,5-dihydro-2,5-dioxo-1H-pyrrol-1-yl)-1-oxohexyl]-L-valyl-N5-(aminocarbonyl)-L-ornithyl]amino]phenyl]methoxy]carbonyl]-N-methyl-L-valyl-N-[(1S,2R)-4-[(2S)-2-[(1R,2R)-3-[[(1R,2S)-2-hydroxy-1-methyl-2-phenylethyl]amino]-1-methoxy-2-methyl-3-oxopropyl]-1-pyrrolidinyl]-2-methoxy-1-[(1S)-1-methylpropyl]-4-oxobutyl]-N-methyl-L-valinamide). DM1 is a derivative of the tubulin inhibitor maytansine while MMAD, MMAE, and MMAF are auristatin derivatives. The preferred payloads of the present invention are selected from the group consisting of mc-MMAF and mc-Val-Cit-PABA-MMAE.

The term "epitope" refers to that portion of a molecule capable of being recognized by and bound by an antibody at one or more of the antibody's antigen-binding regions. Epitopes often consist of a chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody can specifically bind as determined by any method well known in the art, for example, by conventional immunoassays. A "nonlinear epitope" or "conformational epitope" comprises noncontiguous polypeptides (or amino acids) within the antigenic protein to which an antibody specific to the epitope binds.

The term "binding affinity ($K_D$)" as used herein, is intended to refer to the dissociation rate of a particular antigen-antibody interaction. The $K_D$ is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 μM indicates weak binding affinity compared to a $K_D$ of nM. $K_D$ values for antibodies can be determined using methods well established in the art. One method for determining the $K_D$ of an antibody is by using surface plasmon resonance (SPR), typically using a biosensor system such as a Biacore® system.

The term "specifically binds" as used herein in reference to the binding between an antibody and a 5T4 antigen and the antibody binds the 5T4 antigen with a $K_D$ less than about 30 nM as determined by SPR at 25° C.

Pharmaceutically acceptable salt as used herein refers to pharmaceutically acceptable organic or inorganic salts of a molecule or macromolecule.

The term "potency" is a measurement of biological activity and may be designated as $IC_{50}$, or effective concentration of antibody needed to inhibit 50% of growth of a 5T4 positive cell line as described in Example 3. Alternatively, potency may refer to anti-tumor activity as determined in an in vivo tumor xenograph model as shown in Example 4.

The terms "polynucleotide" or "nucleic acid molecule", as used herein, are intended to include DNA molecules and RNA molecules. A nucleic acid molecule may be single-stranded or double-stranded, but preferably is double-stranded DNA.

The polynucleotides that encode the antibodies of the present invention may include the following: only the coding sequence for the variant, the coding sequence for the variant and additional coding sequences such as a functional polypeptide, or a signal or secretory sequence or a pro-protein sequence; the coding sequence for the antibody and non-coding sequence, such as introns or non-coding sequence 5' and/or 3' of the coding sequence for the antibody. The term 'polynucleotide encoding an antibody" encompasses a polynucleotide which includes additional coding sequence for the variant but also a polynucleotide which includes additional coding and/or non-coding sequence. It is known in the art that a polynucleotide sequence that is optimized for a specific host cell/expression system can readily be obtained from the amino acid sequence of the desired protein (see GENEART® AG, Regensburg, Germany).

The polynucleotides encoding the antibodies of the present invention will typically include an expression control polynucleotide sequence operably linked to the antibody coding sequences, including naturally-associated or heterologous promoter regions known in the art. Preferably, the expression control sequences will be eukaryotic promoter systems in vectors capable of transforming or transfecting eukaryotic host cells, but control sequences for prokaryotic hosts may also be used. Once the vector has been incorporated into the appropriate host cell line, the host cell is propagated under conditions suitable for expressing the nucleotide sequences, and, as desired, for the collection and purification of the antibodies. Preferred eukaryotic cell lines include the CHO cell lines, various COS cell lines, HeLa cells, myeloma cell lines, transformed B-cells, or human embryonic kidney cell lines. The most preferred host cell is a CHO cell line.

The present invention encompasses antibodies or antigen-binding portions thereof that bind to a specific epitope on the 5T4 antigen. The epitope identified is a nonlinear or conformational epitope comprising a first contact with the human 5T4 antigen (SEQ ID NO: 11) between amino acid residues 173 and 252 and comprising a second contact between amino acid residues 276 and 355 (see Example 7). Thus, the CDRs and heavy and light chain variable regions described herein are used to make full-length antibodies as well as functional fragments and analogs that maintain the binding affinity of the protein employing the CDRs specific for the above mentioned epitope of the 5T4 antigen.

The binding affinity of antibodies of the present invention is determined using SPR (Example 6). In these experiments the 5T4 antigens are immobilized at low densities onto a BIAcore® chip and antibodies are flowed past. Build up of mass at the surface of the chip is measured. This analytical method allows the determination in real time of both on and off rates to obtain affinity ($K_D$) for binding. The humanized antibodies of the present invention have a $K_D$ of between about 0.30 and about 30 nM; about 0.30 and about 20 nM; about 0.30 and about 10 nM; about 0.5 and about 7 nM; about 1.0 and about 5 nM; and about 1.0 and about 3 nM.

Conjugation of Drugs to an Antibody

The drug has, or is modified to include, a group reactive with a conjugation point on the antibody. For example, a drug can be attached by alkylation (e.g., at the epsilon-amino group lysines or the N-terminus of antibodies), reductive amination of oxidized carbohydrate, transesterification between hydroxyl and carboxyl groups, amidation at amino groups or carboxyl groups, and conjugation to thiols. In some embodiments, the number of drug moieties, p, conjugated per antibody molecule ranges from an average of 1 to 8; 1 to 7, 1 to 6, 1 to 5, 1 to 4, 1 to 3, or 1 to 2. In some embodiments, p ranges from an average of 2 to 8, 2 to 7, 2 to 6, 2 to 5, 2 to 4 or 2 to 3. In other embodiments, p is an average of 1, 2, 3, 4, 5, 6, 7 or 8. In some embodiments, p ranges from an average of about 1 to about 8; about 1 to about 7, about 1 to about 6, about 1 to about 5, about 1 to about 4, about 1 to about 3, or about 1 to about 2. In some embodiments, p ranges from about 2 to about 8, about 2 to about 7, about 2 to about 6, about 2 to about 5, about 2 to about 4 or about 2 to about 3. For examples of chemistries that can be used for conjugation, see, e.g., Current Protocols in Protein Science (John Wiley & Sons, Inc.), Chapter 15 (Chemical Modifications of Proteins) (the disclosure of which is incorporated by reference herein in its entirety.)

For example, when chemical activation of the protein results in formation of free thiol groups, the protein may be conjugated with a sulfhydryl reactive agent. In one aspect, the agent is one which is substantially specific for free thiol groups. Such agents include, for example, malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio.

Linkers

The drug can be linked to an antibody by a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit), a phenylalanine-lysine (phe-lys) linker, or maleimidocapronic-valine-citruline-p-aminobenzyloxycarbonyl (mc-Val-Cit-PABA) linker. Another linker is Sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N-terminus). Yet another linker is maleimidocaproyl (mc). Other suitable linkers include linkers hydrolyzable at a specific pH or a pH range, such as a hydrazone linker. Additional suitable cleavable linkers include disulfide linkers. The linker may be covalently bound to the antibody to such an extent that the antibody must be degraded intracellularly in order for the drug to be released e.g. the mc linker and the like.

A linker can include a group for linkage to the antibody. For example, linker can include an amino, hydroxyl, carboxyl or sulfhydryl reactive groups (e.g., malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio). See generally Wong, Chemistry of Protein Conjugation and Cross-linking; CRC Press, Inc., Boca Raton, 1991.

Immunotherapy

For immunotherapy, an antibody can be conjugated to a suitable drug, such as a cytotoxic or cytostatic agent, an immunosuppressive agent, a radioisotope, a toxin, or the like. The conjugate can be used for inhibiting the multiplication of a tumor cell or cancer cell, causing apoptosis in a tumor or cancer cell, or for treating cancer in a patient. The conjugate can be used accordingly in a variety of settings for the treatment of animal cancers. The conjugate can be used to deliver a drug to a tumor cell or cancer cell. Without being bound by theory, in some embodiments, the conjugate binds to or associates with a cancer-cell or a tumor-associated antigen, and the conjugate and/or drug can be taken up inside a tumor cell or cancer cell through receptor-mediated endocytosis. The antigen can be attached to a tumor cell or cancer cell or can be an extracellular matrix protein associated with the tumor cell or cancer cell. Once inside the cell, one or more specific peptide sequences within the conjugate (e.g., in a linker) are hydrolytically cleaved by one or more tumor-cell or cancer-cell-associated proteases, resulting in release of the drug. The released drug is then free to migrate within the cell and induce cytotoxic or cytostatic or other activities. In some embodiments, the drug is cleaved from the antibody outside the tumor cell or cancer cell, and the drug subsequently penetrates the cell, or acts at the cell surface.

Therapy for Cancer

As discussed above, cancers, including, but not limited to, a tumor, metastasis, or other disease or disorder characterized by uncontrolled cell growth, can be treated or prevented by administration of a protein-drug conjugate.

In other embodiments, methods for treating or preventing cancer are provided, including administering to a patient in need thereof an effective amount of a conjugate and a chemotherapeutic agent. In some embodiments, the chemotherapeutic agent is that with which treatment of the cancer has not been found to be refractory. In some embodiments, the chemotherapeutic agent is that with which the treatment of cancer has been found to be refractory. The conjugate can be administered to a patient that has also undergone a treatment, such as surgery for treatment for the cancer. In another embodiment, the additional method of treatment is radiation therapy.

Multi-Drug Therapy for Cancer

Methods for treating cancer include administering to a patient in need thereof an effective amount of an antibody-drug conjugate and another therapeutic agent that is an anticancer agent. Suitable anticancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, calicheamicin, and docetaxel.

The ADCs of the present invention can be in the form of a pharmaceutical composition for administration that are formulated to be appropriate for the selected mode of administration, and pharmaceutically acceptable diluent or excipients, such as buffers, surfactants, preservatives, solubilizing agents, isotonicity agents, stabilizing agents, carriers, and the like. Remington's Pharmaceutical Sciences, Mack Publishing Co., Easton Pa., 18$^{th}$ ed., 1995, incorporated herein by reference, provides a compendium of formulation techniques as are generally known to practitioners.

These pharmaceutical compositions may be administered by any means known in the art that achieve the generally intended purpose to treat cancer. The preferred route of administration is parenteral, defined herein as referring to modes of administration that include but not limited to intravenous, intramuscular, intraperitoneal, subcutaneous, and intraarticular injection and infusion. The dosage administered will be dependent upon the age, health, and weight of the recipient, kind of concurrent treatment, if any, frequency of treatment, and the nature of the effect desired.

Compositions within the scope of the invention include all compositions wherein an ADC is present in an amount that is effective to achieve the desired medical effect for treating cancer. While individual needs may vary from one patient to another, the determination of the optimal ranges of effective amounts of all of the components is within the ability of the clinician of ordinary skill.

EXAMPLE 1

Preparation of an Anti-5T4 ADC

5T4-A1 antibody drug conjugate (ADC) is prepared via partial reduction of the mAb with tris(2-carboxyethyl)phosphine (TCEP) followed by reaction of reduced Cys residues with the desired maleimide terminated linker-payload. In particular, 5T4-A1 mAb is partially reduced via addition of 2.8 molar excess of tris(2-carboxyethyl)phosphine (TCEP) in 100 mM HEPES (4-(2-hydroxyethyl)-1-piperazineethanesulfonic acid buffer), pH 7.0 and 1 mM diethylenetriaminepentaacetic acid (DTPA) for 2 h at 37° C. The desired linker-payload is then added to the reaction mixture at a linker-payload/mAb-thiol molar ratio of 5.5 (maleimidocapronic-monomethylauristatin F [mc-MMAF]) or 8 (maleimidocapronic-valine-citruline-p-aminobenzyloxycarbonyl-monomethylauristatin E [mc-Val-Cit-PABA-MMAE]) and reacted for an additional 1 h at 25° C. in the presence of 15% v/v of dimethylacetamide (DMA). After the 1 h incubation period, N-ethylmaleimide (4.5 fold excess for mc-MMAF and 2 fold excess for mc-Val-Cit-PABA-MMAE) is added to cap the unreacted thiols and is allowed to react for 15 minutes followed by addition of 6 fold excess L-Cys to quench any unreacted linker-payload. The reaction mixture is dialyzed overnight at 4° C. in phosphate buffered saline (PBS), pH 7.4, and purified via SEC (AKTA explorer, Superdex 200 10/30 GL column). The ADC is further characterized via size exclusion chromatography (SEC) for purity, hydrophobic interaction chromatography (HIC), and liquid chromatography electrospray ionisation tandem mass spectrometry (LC-ESI MS) to calculate loading, and the concentration is determined via UV spectrophotometer.

EXAMPLE 2

Binding Studies

Cells expressing the 5T4 antigen, and the negative control Raji cells, are plated at a density of 500,000 cells/well on non-tissue culture treated 96 well plates and kept on ice. Dilutions of the A1 and A1-IgG4 antibodies or A1-mcMMAF ADC are made in 3% bovine serum albumin BSA in Dulbecco's phosphate buffered saline (DPBS) and added to the plate at a final concentration of 10 μg/mL. The plates are then incubated on ice for 1 hour followed by 2 washes. The secondary antibody, PE (phycoerythrin) conjugated Goat Anti-Human IgG Fc is added to the wells. After 30 minutes of incubation at 4° C., the mean fluorescence intensity is then measured using a flow cytometer.

The data in Table 4 indicates that the A1 antibody binds a diverse panel of 5T4 positive cell lines. The data in Table 5 indicates that similar binding on several different cell lines is observed with the A1 and A1-IgG4 antibodies as well as the A1-mcMMAF ADC.

TABLE 4

| Human Cell Lines | A1 antibody Mean Fluorescent Intensity |
|---|---|
| MDAMB435/5T4 (melanoma) | 15000 |
| MDAMB468 (breast) | 3000 |
| MDAMD361-DYT2 (breast) | 4500 |
| NCI-H157 (lung) | 4100 |
| A431 (epithelial) | 2000 |
| Caki (kidney) | 2500 |
| PC3mm2 (prostate) | 4500 |
| PC14PE6 (lung) | 3200 |
| Panc1 (pancreatic) | 3500 |
| BxPC3 (pancreatic) | 1000 |
| Su8686 (pancreatic) | 3700 |
| H1975 | 1600 |
| 37622A-(Primary Lung cancer cells) | 10600 |
| Raji (negative control) | <100 |

TABLE 5

| | Mean Fluorescent Intensity | | | | |
|---|---|---|---|---|---|
| Cell Lines | A1 | A1-mcMMAF | A1-IGG4 | A1-IGG4-CM | IgG control |
| MDAMD361-DYT2 | 7000 | 6900 | 5500 | 4800 | <100 |
| A431 | 3900 | 3400 | 2400 | 2000 | <100 |
| MDAMB468 | 3500 | 2800 | 2500 | 1800 | <100 |
| PC3mm2 | 3400 | 2700 | 2100 | 1500 | <100 |
| Raji | <200 | <200 | <200 | <100 | <100 |

EXAMPLE 3

Cytotoxicity Assay

Cell lines expressing 5T4, and the negative control Raji cell line, are cultured with increasing concentrations of ADC. After four days, viability of each culture is assessed. $IC_{50}$ values are calculated by logistic non-linear regression and are presented as ng Ab/mL. A1-mcMMAF, A1-vcMMAE, A3-mcMMAF and A3-mcMMAE are shown to inhibit the growth of 5T4 expressing cell lines (MDAMB435/5T4, MDAMB468, and MDAMB361DYT2), while being inactive on 5T4 negative cells (Raji), Table 6.

TABLE 6

| | $IC_{50}$ (ng Ab/ml) | | | |
|---|---|---|---|---|
| ADC | MDAMB435/5T4 | MDAMB361DYT2 | MDAMB468 | Raji (5T4-) |
| A1-mcMMAF | 1.3 | 104.2 | 534.2 | >45,000 |
| A1-vcMMAE | 6.8 | 157.7 | 7667 | >45,000 |
| A3-mcMMAF | 0.3 | 31.0 | 27.7 | >45,000 |
| A3-vcMMAE | 3.5 | 86.8 | 160.6 | >45,000 |
| Nonbinding Ab-mcMMAF | 21258 | ~50,000 | 73059 | >45,000 |
| Nonbinding Ab-vcMMAE | 7979 | 27650 | 23819 | >45,000 |

Additionally, 5T4+ primary lung tumor 37622a cells are isolated and grown in culture. Cells are cultured with increasing concentrations of ADC. Ten days later, viability of each culture is assessed using the MTS method. $IC_{50}$ values are calculated by logistic non-linear regression and are presented as ng Ab/ml. A1-mcMMAF, A1-vcMMAE, A3-mcMMAF, and A3-vcMMAE inhibit the growth of the primary lung tumor cells, Table 7.

TABLE 7

| ADC | 37622a primary lung $IC_{50}$ (ng Ab/ml) |
|---|---|
| A1-mcMMAF | 504.1 |
| A1-vcMMAE | 443.1 |
| A3-mcMMAF | 77.2 |
| A3-vcMMAE | 78.1 |
| Nonbinding Ab-mcMMAF | >45,000 |

EXAMPLE 4

Subcutaneous Xenograft Model

Female, athymic (nude) mice (or another strain of immunosuppressed mice) are injected s.c. with MDAMB435/5T4, MDAMB361 DYT2, or H1975 tumor cells. Mice with staged tumors, approximately 0.1 to 0.3 g (n=6 to 10 mice/treatment group) are administered intravenously Q4D×4 with normal saline (vehicle), A1-mcMMAF, A1-vcMMAE, A1-mcMMAD, A1-smccDM1, A3-mcMMAF, A3-vcMMAE, or a nonbinding control antibody conjugated to either mcMMAF or vcMMAE, at the dose of 3 mg Ab/kg. All ADCs are dosed based on Ab content. Tumors are measured at least once a week and their size (mm²±SEM) is calculated as mm²=0.5× (tumor width²)×(tumor length).

The data in Table 8 indicates that A1-mcMMAF, A1-vcMMAE, A1-vcMMAD, A3-mcMMAF, and A3-vcMMAE inhibit the growth of MDAMB435/5T4 xenografts while A1-mcMMAD and A1-smccDM1 were not active in this model.

The data in Table 9 indicates that A1-mcMMAF, A1-vcMMAE, A1-vcMMAD, A1-smccDM1, A3-mcMMAF, and A3-vcMMAE inhibit the growth of MDAMB361 DYT2 xenografts while A1-mcMMAD was not active in this model.

The data in Table 10 indicates that A1-mcMMAF, A1-vcMMAE, A1-vcMMAD, A3-mcMMAF, and A3-vcMMAE inhibit the growth of H1975 xenografts while A1-mcMMAD and A1-smccDM1 were not active in this model.

TABLE 8

| Compound (3 mg/kg Q4dx4) | MDAMB435/5T4 xenografts Tumor volume (mm³, x ± sem) | | | | |
|---|---|---|---|---|---|
| | Day 0 | Day 17 | Day 42 | Day 65 | Day 85 |
| Vehicle | 169 ± 8 | 531 ± 73 | 1255 ± 190 | GT | GT |
| A1 mcMMAF | 168 v 15 | 53 ± 12 | 67 ± 56 | 174 ± 119 | 364 ± 278 |
| A1 vcMMAE | 168 ± 8 | 4 ± 4 | 10 ± 10 | 91 ± 91 | 200 ± 200 |
| A1 mcMMAD | 168 ± 12 | 390 ± 112 | GT | GT | GT |
| A1 smccDM1 | 174 ± 10 | 429 ± 62 | 1255 ± 227 | 1781 ± 388 | GT |
| A1 vcMMAD | 169 ± 12 | 17 ± 7 | 0 ± 0 | 0 ± 0 | 0 ± 0 |
| A3 mcMMAF | 174 ± 12 | 105 ± 27 | 216 ± 143 | 448 ± 220 | GT |
| A3 vcMMAE | 172 ± 13 | 0 ± 0 | 0 ± 0 | 0 ± 0 | 0 ± 0 |
| Nonbinding Ab mcMMAF | 170 ± 11 | 100 ± 15 | 314 ± 121 | 838 ± 381 | GT |
| Nonbinding Ab vcMMAE | 172 ± 11 | 168 ± 53 | 461 ± 178 | GT | GT |

GT=group terminated due to large tumor size

TABLE 9

| Compound (3 mg/kg Q4dx4) | MDAMB361 DYT2 xenografts Tumor volume (mm³, x ± sem) | | | | |
|---|---|---|---|---|---|
| | Day 0 | Day 19 | Day 47 | Day 90 | Day 131 |
| Vehicle | 353 ± 10 | 363 ± 58 | 558 ± 149 | 1117 ± 348 | GT |
| A1 mcMMAF | 348 ± 14 | 76 ± 32 | 0 ± 0 | 7 ± 7 | 11 ± 11 |
| A1 vcMMAE | 356 ± 11 | 86 ± 8 | 0 ± 0 | 9 ± 9 | 34 ± 27 |
| A1 vcMMAD | 352 ± 26 | 130 ± 15 | 0 ± 0 | 0 ± 0 | 0 ± 0 |
| A3 mcMMAF | 342 ± 23 | 128 ± 10 | 79 ± 30 | 105 ± 49 | 353 ± 234 |
| A3 vcMMAE | 354 ± 21 | 111 ± 20 | 21 ± 21 | 72 ± 72 | 155 ± 155 |
| A1 mcMMAD | 347 ± 15 | 380 ± 66 | 775 ± 199 | GT | GT |
| A1 vcMMAD | 352 ± 26 | 130 ± 15 | 0 ± 0 | 0 ± 0 | 0 ± 0 |
| A1 smccDM1 | 353 ± 25 | 123 ± 9 | 51 ± 25 | 98 ± 41 | 330 ± 146 |
| Nonbinding Ab mcMMAF | 342 ± 38 | 407 ± 93 | 869 ± 198 | GT | GT |
| Nonbinding Ab vcMMAE | 344 ± 20 | 303 ± 78 | 346 ± 185 | 595 ± 362 | GT |

GT = group terminated due to large tumor size

TABLE 10

| Compound | Dose (mg/kg) Q4dx4 | H1975 Xenografts Tumor volume (mm³, x ± sem) | | | | |
|---|---|---|---|---|---|---|
| | | Day 0 | Day 8 | Day 15 | Day 22 | Day 40 |
| Vehicle | | 423 ± 14 | 1154 ± 136 | 2229 ± 240 | GT | GT |
| A1 mcMMAF | 3 | 425 ± 14 | 619 ± 46 | 519 ± 45 | 581 ± 79 | 2840 ± 207 |
| A1 vcMMAE | 3 | 425 ± 12 | 702 ± 45 | 929 ± 90 | 926 ± 116 | GT |
| A1 vcMMAD | 3 | 427 ± 18 | 739 ± 59 | 467 ± 19 | 240 ± 14 | 625 ± 317 |
| A3 mcMMAF | 3 | 426 ± 10 | 980 ± 79 | 1343 ± 140 | 1261 ± 203 | GT |
| A3 vcMMAE | 3 | 431 ± 14 | 944 ± 52 | 993 ± 71 | GT | GT |
| A1 mcMMAD | 3 | 427 ± 16 | 837 ± 69 | 1468 ± 139 | GT | GT |
| A1 smccDM1 | 3 | 423 ± 18 | 901 ± 83 | 1852 ± 167 | GT | GT |
| Nonbinding Ab-mcMMAF | 3 | 423 ± 16 | 1026 ± 68 | 1861 ± 224 | GT | GT |
| Nonbinding Ab-vcMMAE | 3 | 427 ± 13 | 1213 ± 67 | 1959 ± 139 | GT | GT |

GT = group terminated due to large tumor size

Alternatively, nude mice with 37622a primary tumor cell xenografts established subcutaneously are treated iv Q4D×4 with A1-mcMMAF, A1-mcMMAD, A1-vcMMAD, or A3-mcMMAF at the dose of 3 mg Ab/kg and the tumor growth is monitored over the period of 96 days. Table 11 demonstrates that A1-mcMMAF, A1-vcMMAD and A3-mcMMAF inhibit the growth of 37622a primary tumor xenografts compared to vehicle control treated animals while A1-mcMMAD was not active in this model.

TABLE 11

37622a Primary Tumor Xenografts
Tumor volume (mm³, x ± sem)

| Compound | Dose (mg/kg) Q4dx4 | Day 1 | Day 22 | Day 46 | Day 68 | Day 96 |
|---|---|---|---|---|---|---|
| Vehicle | | 111 ± 18 | 503 ± 155 | 1174 ± 247 | GT | GT |
| A1-mcMMAF | 3 | 111 ± 18 | 67 ± 11 | 124 ± 47 | 233 ± 105 | 357 ± 150 |
| A1-mcMMAD | 3 | 127 ± 28 | 376 ± 119 | 862 ± 377 | GT | GT |
| A1-vcMMAD | 3 | 108 ± 14 | 52 ± 14 | 13 ± 5 | 50 ± 37 | 160 ± 121 |
| A3-mcMMAF | 3 | 131 ± 28 | 99 ± 26 | 211 ± 128 | 463 ± 210 | GT |

GT = group terminated due to large tumor size

Unexpectedly, the data in Tables 8-11 show that ADCs with the same antibody and drug payload but with different linkers had a dissimilar efficacy profile i.e. A1-mcMMAD vs A1-vc-MMAD in all four xenograft models. In addition, the data show that ADCs with the same antibody and linker but with different drug payloads also had a different efficacy profile i.e. A1-mcMMAF vs A1-mcMMAD, in all four xenograft models. Thus, the drug MMAD is effective in all four xenograft models when linked to the A1 antibody by the vc linker but has no activity in any of the xenograft models tested when linked by the mc linker. In contrast, the drug MMAF is highly effective in all 4 xenograft models when linked to the A1 antibody with the mc linker while the chemically related drug MMAD has no activity in all 4 xenograft models when linked to the same antibody by the same linker.

Yet another unexpected observation is seen with the ADC A1-smccDM1 (Tables 8-10). This ADC was very effective against the MDAMB361 DYT2 xenograft but had essentially no effect against the MDAMB435/5T4 and the H1975 xenografts even though all the xenografts have a high expression of the 5T4 target antigen. This data illustrates that the effectiveness of the linker-payload could not be predicted even when the same high affinity antibody is utilized or even when the same ADC is used.

EXAMPLE 5

Antibody Dependent Cell-Mediated Cytotoxicity (ADCC)

ADCC Assay:

Blood from a healthy volunteer is collected into a BD Vacutainer CPT cell preparation tube with sodium heparin. Human peripheral blood mononucleocytes (PBMC) are harvested and resuspended in assay buffer (RPMI 1640 supplemented with 10 mM HEPES) at $2.5 \times 10^7$ cells/ml. Target cells (MDAMB435/5T4 or MDAMB435/neo) are seeded at a density of $1 \times 10^4$ cells/well in a 96 well assay plate. A1 antibody or A1-mcMMAF are added, then human PBMC effector cells ($5 \times 10^5$) are dispensed into the wells for an effector:target cell ratio (E:T) of 50:1. The assay plate is incubated at 37° C. for 4 hours for ADCC activity. The plate is harvested by adding equal volume of CytoTox-One reagent (Promega). Stop solution (Promega; 50 ul) is added to each well and lactate dehydrogenase release was quantified by measuring fluorescence intensity. As a positive control, 2 µl of lysis buffer per well is added to generate a maximum LDH release (100% cytotoxicity) in control wells. Percent cytotoxicity is calculated using the following equation:

$$\% \text{ Specific Cytotoxicity} = \frac{\text{experimental} - \text{effector spontaneous} - \text{target spontaneous}}{\text{target maximum} - \text{target spontaneous}} \times 100$$

Where "experimental" corresponds to the signal measured in one of the experimental conditions, "effector spontaneous" corresponds to the signal measured in the presence of PBMC alone, "target spontaneous" corresponds to the signal measured in the presence of target cells alone, and "target maximum" corresponds to the signal measured in the presence of detergent-lysed target cells alone.

The ADCC activity of A1-IgG1 Ab and A1-mcMMAF compared to A1-IgG4 Ab is shown in Table 12. Both the A1 antibody and A1-mcMMAF demonstate comparable ADCC activity indicating that the ADCC activity of A1-mcMMAF may contribute to its anti-tumor activity.

TABLE 12

| Compound | % Cytotoxicity |
|---|---|
| A1-IgG1 | 37 ± 8 |
| A1-mcMMAF | 34 ± 1 |
| A1-IgG4 | 9 ± 5 |

EXAMPLE 6

Binding Affinity

Surface plasmon resonance (SPR) analysis is performed utilizing the BIAcore® to determine the affinity constants for A1-IgG1 and A1-IgG4 binding to either human or cynomolgus 5T4 at pH 6.0 and pH 7.4. BIAcore® technology utilizes changes in the refractive index at the surface layer upon binding of the huA1 antibody variants to the human 5T4 protein immobilized on the surface layer. Binding is detected by SPR of laser light refracting from the surface. Analysis of the signal kinetics on-rate and off-rate allows the discrimination between non-specific and specific interactions. The 5T4 proteins used for this analysis consisted of the human or cynomolgus 5T4 ectodomain fused to the human IgG1-Fc domain and low densities (45.1 and 45.4 RU for human and cynomolgus respectively) are immobilized onto a CM5 chip to accurately measure affinity constants.

The measurement of specific binding to the 5T4 ectodomain is attained by subtracting binding to a reference surface that had only human IgG1-Fc protein immobilized onto the CM5 chip at the same density to that on the 5T4-Fc surfaces. Next, various concentrations of A1, A1-IgG4, or A3 antibodies in either HBS-EP pH 7.4 or MES-EP pH 6.0 buffer are injected over the surface. The surface is regenerated two times with Glycine pH 1.7+0.05% Surfactant P20 (GE Healthcare, BR-1000-54) between injection cycles.

Results show that the A1 has a slightly higher affinity for human 5T4 using the low-density 5T4 surface at both pH 6.0 and pH 7.4 relative to A1-IgG4 (1.5-fold and 1.2-fold respectively, Table 13). Additionally, A1 exhibited slightly better binding to cynomolgus 5T4 at both pH 6.0 and pH 7.4 compared to A1-IgG4 (1.7-fold and 1.2-fold respectively) and both A1 and A1-IgG4 bound human 5T4, 3-4 fold better than cynomolgus 5T4 (Table 12).

TABLE 13

| Antibody | Antigen | pH | ka (1/Ms) | kd (1/s) | KD (nM) |
|---|---|---|---|---|---|
| A1-IgG1 | hu5T4 | 6.0 | 4.31E+05 | 4.59E−04 | 1.06 |
| A1-IgG4 | hu5T4 | 6.0 | 6.26E+05 | 8.93E−04 | 1.43 |
| A1-IgG1 | cyno5T4 | 6.0 | 2.33E+05 | 6.41E−04 | 2.76 |
| A1-IgG4 | cyno5T4 | 6.0 | 2.02E+05 | 9.50E−04 | 4.70 |
| A1-IgG1 | hu5T4 | 7.4 | 2.75E+05 | 1.32E−04 | 0.48 |
| A1-IgG4 | hu5T4 | 7.4 | 3.28E+05 | 1.72E−04 | 0.52 |
| A1-IgG1 | cyno5T4 | 7.4 | 1.51E+05 | 2.73E−04 | 1.80 |
| A1-IgG4 | cyno5T4 | 7.4 | 1.81E+05 | 3.82E−04 | 2.11 |

Comparing the A1 and A3 antibodies, it is apparent that the A1 antibody binds human and cynomolgus 5T4 better at pH 7.4 relative to pH 6.0 while the A3 antibody exhibits enhanced binding at pH 6.0 compared to pH 7.4, Table 14.

TABLE 14

| Antibody | Antigen | pH | ka (1/Ms) on | kd (1/s) off | KD (nM) |
|---|---|---|---|---|---|
| A1 | hu5T4 | 6.0 | 4.31E+05 | 4.59E−04 | 1.06 |
| A3 | hu5T4 | 6.0 | 3.51E+05 | 4.17E−05 | 0.12 |
| A1 | cyno5T4 | 6.0 | 2.33E+05 | 6.41E−04 | 2.76 |
| A3 | cyno5T4 | 6.0 | 4.58E+05 | 1.87E−04 | 0.41 |
| A1 | hu5T4 | 7.4 | 2.75E+05 | 1.32E−04 | 0.48 |
| A3 | hu5T4 | 7.4 | 1.79E+05 | 3.06E−05 | 0.17 |
| A1 | cyno5T4 | 7.4 | 1.51E+05 | 2.73E−04 | 1.80 |
| A3 | cyno5T4 | | 1.98E+05 | 1.62E−04 | 0.82 | 1.98E+05 |

EXAMPLE 7

Epitope Mapping Using 5T4 Chimeras

To identify the epitopes to which each of the A1 and A3 antibodies bind, an enzyme linked immunosorbent assay (ELISA) is performed using (1) 5T4 ectodomain Fc construct and (2) human/mouse 5T4 chimera constructs transiently expressed in COS-1 cells. The ectodomain includes the amino-terminal region, two leucine-rich repeats, and the intervening hydrophilic region. Mouse and rat 5T4 ectodomains contain a 6 amino acid direct repeat within their hydrophilic region.

Fusion proteins containing a 5T4 ectodomain and a Fc constant region from human IgG1 are prepared using human 5T4 (amino acids 1-355), mouse 5T4 (amino acids 1-361), rat 5T4 (amino acids 1-361), cynomologus monkey 5T4 (amino acids 1-355), chimpanzee 5T4 (amino acids 1-355), and black-tailed marmoset (amino acids 1-355). The binding results with human/mouse 5T4 chimera constructs are summarized in Table 14, which indicates specific binding, partial binding, or lack of binding, by the A1 and A3 antibodies.

Table 15 refers to binding ability of the antibodies to the various human/mouse chimeras and the nomenclature is designated by mouse 5T4 content. When no binding is observed, this indicates where the antibody binds human 5T4 since these antibodies do not bind mouse 5T4. For example, the A3 antibody has the most N-terminal binding epitope (between 83-163) and this is shown by lack of binding to the 5T4 chimera that has residues 83-163 replaced by mouse 5T4, hence A3 can no longer bind. Based upon these results, it is determined that humanized A1 antibody has a first contact with human 5T4 between amino acid residues 173 and 252 and a second contact with human 5T4 between amino acid residues 276 and 355. The A3 antibody binds the first leucine-rich repeat region of human 5T4 between amino acid residues 83 through 163. The number of amino acid residues corresponds to the human 5T4 antigen amino acid sequence of SEQ ID NO: 11.

TABLE 15

| | Antibody | |
|---|---|---|
| 5T4 Antigen Construct | A1 | A3 |
| Human/mouse 83-163 | + | − |
| Human/mouse 173-361 | − | + |
| Human/mouse 173-258 | +/− | + |
| Human/mouse 282-361 | +/− | + |

EXAMPLE 8

Comparison of A1-mcMMAF ADC with A1-IgG4-CM ADC

A1-mcMMAF is compared to A1-IgG4-AcBut calicheamicin (A1-IGG4-CM) for both safety and efficacy. A1-4-CM is comprised of the A1-IgG4 antibody conjugated with the linker, AcBut [-(4' acetylphenoxy) butanoic acid], to a calicheamicin payload. The calicheamicins are potent antitumor agents of a class of enediyne antibiotics derived from the bacterium *Micromonospora echinospora*.

The cell binding activity of A1 Ab, A1-IgG4 Ab, A1-mc-MMAF ADC and A1-IgG4-CM ADC are compared using several 5T4 positive cell lines (see Example 2, Table 5). The data indicates that similar binding is observed with the A1 and A1-IgG4 antibodies as well as the A1-mcMMAF ADC, all of which have a higher mean fluorescent intensity than A1-IgG4-CM for all the 5T4 positive cell lines tested.

A1-mcMMAF and A1-IgG4-CM are tested side-by-side in the MDAMB435/5T4 subcutaneous xenograft model. Both ADCs are given iv (Q4d×2) when the tumors reach approximately 200 mm² in size. The anti-tumor activity of A1-IgG4-CM at a dose of 3 mg/kg is similar to the anti-tumor activity of A1-mcMMAF administered at dose of 10 mg/kg (Table 16). Based upon these results, the anti-tumor activity of A1-IgG4-CM is approximately 3.3 fold more potent than A1-mcMMAF.

TABLE 16

| | Dose (mg/kg) | Tumor volume (mm³, x ± sem) | | | | |
|---|---|---|---|---|---|---|
| Compound | Q4dx4 | Day 0 | Day 7 | Day 21 | Day 31 | Day 45 |
| Vehicle | 0 | 123 ± 8 | 195 ± 36 | 402 ± 56 | 635 ± 111 | 1309 ± 332 |
| A1-mcMMAF | 3 | 124 ± 11 | 121 ± 8 | 166 ± 29 | 227 ± 42 | 361 ± 89 |
| A1-mcMMAF | 10 | 123 ± 14 | 76 ± 11 | 0 ± 0 | 3 ± 3 | 2 ± 1 |
| A1-IGG4-CM | 3 | 121 ± 12 | 140 ± 15 | 32 ± 10 | 24 ± 10 | 26 ± 15 |

It could be expected that the 3.3 fold enhanced potency of A1-IgG4-CM over that of A1-mcMMAF would translate into a 3.3 fold enhanced safety margin of A1-mcMMAF over that of A1-IgG4-CM in an animal toxicity study. However, when the safety profile of A1-IgG4-CM in cynomolgus macques is reviewed, it is determined that A1-IgG4-CM is at least 100 fold more toxic than A1-mcMMAF in the cynomolgus macque. When A1-IgG4-CM is administered at 0.032, 0.095 and 0.32 mg Ab/kg/cycle (2, 6, 20 μg calicheamicin/kg/cycle) to male (n=3) and female (n=3) cynomolgus macques, toxicity is observed at each dose level. After 2 cycles (2 doses), 4 out of 6 animals in the 0.095 treatment group are either euthanized or found dead. On the other hand, no deaths are observed at dosages up to 10 mg/kg with A1-mcMMAF (247 μg mcMMAF/kg/cycle), after 2 cycles (2 doses), over the same 4 week time period. In summary, the 10 mg/kg dosage group of A1-mcMMAF is safe while the 0.096 mg/kg dosage group of A1-IgG4-CM is deemed toxic when both are administered twice to cynomolgus macques in a 4 week observation period.

Unexpectedly, these results demonstrate a 105 fold (10/0.095=105) safety margin of A1-mcMMAF over that of A1-IgG4-CM, rather than the expected 3.3 fold safety margin based on the relative anti-tumor potency of each ADC. This data reveals the unpredictable nature of antibody-drug conjugates that utilize antibodies to the same antigen target but are conjugated to a different drug payload.

EXAMPLE 9

A1-mcMMAF Mouse PK/PD Modeling and Clinical Dose Predictions

PK/PD modeling has been used to quantify the tumor response of A1-mcMMAF in mouse xenograft studies, in order to determine efficacious concentration across cell lines. The transit compartment tumor kill PK/PD model used was previously described by Simeoni et al. (Simeoni et al, *Cancer Res*, 64:1094, (2004). The model has been modified to account for linear, exponential and logistic growth of tumor, and saturative killing by the drug. PK/PD model parameters include:

| | |
|---|---|
| $k_{g\,ex}$ | exponential growth |
| $k_g$ | logistic growth |
| $w_0$ | initial tumor volume |
| tau | transduction rate |
| $k_{max}$ | maximum kill rate |
| $kC_{50}$ | concentration at half max kill rate |

The PK/PD modeling results are used to calculate the Tumor Static Concentration (TSC, Equation 1). This is the drug concentration where tumor growth is equal to tumor death rates and tumor volume remains unchanged. TSC can be defined as the minimal concentration required for efficacy. TSC is used to give guidance on clinical dose selection, with concentrations of >TSC required for efficacy in the clinic.

For A1-mcMMAF, mouse PK was determined in a separate study (3 mg/kg IV, female athymic nu/nu mice). Mouse xenograft studies were completed using 3 different 5T4 cell lines with A1-mcMMAF administered at dose levels between 1 and 30 mg/kg every 4 days: cell line MDAMB435/5T4 (dosed at 1, 3, 10, and 30 mg/kg), cell line H1975 (dosed at 1, 3, and 10 mg/kg) and cell line 37622A (dosed at 1 and 10 mg/kg). PK/PD modeling was performed as described and TSCs are reported in Table 17.

Mouse PK/PD parameters for each xenograft cell line were combined with predicted human PK of A1-mcMMAF to simulate doses required for efficacy in the clinic. Using this methodology, A1-mcMMAF has a predicted minimally efficacious clinical dose of about 0.22 to about 2.3 mg/kg Q3 weeks [every three weeks] (Table 17).

In an embodiment of the present invention, dose ranges can be in the range from about 0.18 mg/kg to about 2.7 mg/kg, from about 0.22 mg/kg to about 2.6 mg/kg, from about 0.27 mg/kg to about 2.5 mg/kg, from about 0.32 mg/kg to about 2.3 mg/kg, from about 0.37 mg/kg to about 2.15 mg/kg, from about 0.42 mg/kg to about 2.10 mg/kg, from about 0.47 mg/kg to about 2.05 mg/kg, from about 0.52 mg/kg to about 2.00 mg/kg, from about 0.57 mg/kg to about 1.95 mg/kg, from about 0.62 mg/kg to about 1.90 mg/kg, from about 0.67 mg/kg to about 1.85 mg/kg, from about 0.72 mg/kg to about 1.80 mg/kg, from about 0.82 mg/kg to about 1.70 mg/kg, from about 0.92 mg/kg to about 1.60 mg/kg, from about 1.02 mg/kg to about 1.50 mg/kg, from about 1.12 mg/kg to about 1.40 mg/kg, or from about 1.20 mg/kg to about 1.30 mg/kg, with dosing at Q3 weeks. Preferably, dose ranges can be in the range from about 0.22 mg/kg to about 2.3 mg/kg.

Equation 1

$$\text{If } \frac{k_{gEx}}{k_g} w_0 \leq 1, \quad TSC = \frac{k_{gEx} \cdot k_{C50}}{k_{max} - k_{gEx}} \quad 1.1$$

$$\text{If } \frac{k_{gEx}}{k_g} w_0 > 1, \quad TSC = \frac{k_g \cdot k_{C50}}{w_0 \cdot k_{max} - k_g} \quad 1.2$$

TABLE 17

| Cell Line | TSC [80% confidence] (ug/ml) | Predicted Stasis Dose [80% confidence] (mg/kg Q3 weeks) |
|---|---|---|
| MDAMB435/5T4 | 1.1 [0.9, 1.4] | 0.22 [0.18, 0.28] |
| 37622A | 5.1 [2.1, 9.9] | 1.1 [0.6, 2.0] |
| H1975 | 11.6 [9.6, 14.1] | 2.3 [2.0, 2.7] |

We claim:

1. An antibody-drug conjugate of the formula:

Ab-(LU-D)p or a pharmaceutically acceptable salt thereof wherein:
   (a) Ab is an anti-5T4 antibody or antigen binding portion thereof, comprising a heavy chain having SEQ ID NO: 1 and a light chain having SEQ ID NO: 2,
   (b) LU is a linker unit selected from the group consisting of maleimidocaproyl and maleimidocaproyl-Val-Cit,
   (c) p is an integer from about 1 to about 8, and
   (d) D is a Drug unit selected from the group consisting of MMAE, MMAD, and MMAF.

2. The antibody-drug conjugate of claim 1, wherein said antibody or antigen binding portion thereof, recognizes an epitope on human 5T4 antigen, wherein said epitope comprises amino acid residues 173-258 and 282-361 of the amino acid sequence of SEQ ID NO:11.

3. The antibody-drug conjugate of claim 1 wherein:
   (a) said anti-5T4 antibody consists of a heavy chain having SEQ ID NO: 1 and a light chain having SEQ ID NO: 2,
   (b) said LU is maleimidocaproyl,
   (c) said Drug is MMAF, and
   (d) p is 4.

4. A pharmaceutical composition comprising the antibody-drug conjugate of claim 1 and a pharmaceutically acceptable carrier.

5. A method of treating 5T4-positive cancer in a patient in need thereof, comprising administering to said patient the antibody-drug conjugate according to claim 1.

6. The method of claim 5 wherein said cancer is selected from the group consisting of colorectal, breast, pancreatic, and non-small cell lung carcinomas.

* * * * *

SEQUENCE LISTING

<160> NUMBER OF SEQ ID NOS: 34

<210> SEQ ID NO 1
<211> LENGTH: 449
<212> TYPE: PRT
<213> ORGANISM: Artificial Sequence
<220> FEATURE:
<223> OTHER INFORMATION: "Synthetic Sequence Humanized A1 human IgG1 heavy chain

<400> SEQUENCE: 1

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Asn Phe
            20                  25                  30

Gly Met Asn Trp Val Arg Gln Ala Pro Gly Lys Gly Leu Glu Trp Val
        35                  40                  45

Ala Trp Ile Asn Thr Asn Thr Gly Glu Pro Arg Tyr Ala Glu Glu Phe
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Asp Gly Ala Tyr Phe Phe Asp Tyr Trp Gly Gln Gly
           100                 105                 110

Thr Leu Val Thr Val Ser Ser Ala Ser Thr Lys Gly Pro Ser Val Phe
       115                 120                 125

Pro Leu Ala Pro Ser Ser Lys Ser Thr Ser Gly Gly Thr Ala Ala Leu
   130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 2
<211> LENGTH: 214
<212> TYPE: PRT
<213> ORGANISM: Artificial Sequence
<220> FEATURE:
<223> OTHER INFORMATION: Synthetic Sequence Humanized A1 human Kappa
      light chain

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Phe Ala Thr Asn Arg Tyr Thr Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 119
<212> TYPE: PRT
<213> ORGANISM: Artificial Sequence
<220> FEATURE:

-continued

<223> OTHER INFORMATION: Synthetic Sequence A1-VH

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Phe
            20                  25                  30

Gly Met Asn Trp Val Arg Gln Ala Pro Gly Lys Gly Leu Glu Trp Val
        35                  40                  45

Ala Trp Ile Asn Thr Asn Thr Gly Glu Pro Arg Tyr Ala Glu Glu Phe
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Asp Gly Ala Tyr Phe Phe Asp Tyr Trp Gly Gln Gly
            100                 105                 110

Thr Leu Val Thr Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: Synthetic Sequence A1-VL

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Phe Ala Thr Asn Arg Tyr Thr Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Trp
                85                  90                  95

Thr Phe Gly Gln Gly Thr Lys Val Glu Ile Lys
            100                 105

<210> SEQ ID NO 5
<211> LENGTH: 5
<212> TYPE: PRT
<213> ORGANISM: Artificial Sequence
<220> FEATURE:
<223> OTHER INFORMATION: Synthetic Sequence A1-HC CDR1

<400> SEQUENCE: 5

Asn Phe Gly Met Asn
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic Sequence A1-HC CDR2

```
<400> SEQUENCE: 6

Trp Ile Asn Thr Asn Thr Gly Glu Pro Arg Tyr Ala Glu Glu Phe Lys
1               5                   10                  15

Gly

<210> SEQ ID NO 7
<211> LENGTH: 10
<212> TYPE: PRT
<213> ORGANISM: Artificial Sequence
<220> FEATURE:
<223> OTHER INFORMATION: Synthetic Sequence A1-HC CDR3

<400> SEQUENCE: 7

Asp Trp Asp Gly Ala Tyr Phe Phe Asp Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Sequence A1-LC-CDR1

<400> SEQUENCE: 8

Lys Ala Ser Gln Ser Val Ser Asn Asp Val Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Sequence A1-LC-CDR2

<400> SEQUENCE: 9

Phe Ala Thr Asn Arg Tyr Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Sequence A1-LC-CDR3

<400> SEQUENCE: 10

Gln Gln Asp Tyr Ser Ser Pro Trp Thr
1               5

<210> SEQ ID NO 11
<211> LENGTH: 420
<212> TYPE: PRT
<213> ORGANISM: Artificial Sequence
<220> FEATURE:
<223> OTHER INFORMATION: Synthetic Sequence Human 5T4 antigen

<400> SEQUENCE: 11

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Pro Thr Ser Ser Ala Ser Ser Phe Ser Ser Ser Ala Pro Phe Leu
        35                  40                  45

Ala Ser Ala Val Ser Ala Gln Pro Pro Leu Pro Asp Gln Cys Pro Ala
    50                  55                  60
```

```
Leu Cys Glu Cys Ser Glu Ala Ala Arg Thr Val Lys Cys Val Asn Arg
 65                  70                  75                  80

Asn Leu Thr Glu Val Pro Thr Asp Leu Pro Ala Tyr Val Arg Asn Leu
                 85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160

Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
        275                 280                 285

Val Phe Leu Asp Asn Asn Pro Trp Val Cys Asp Cys His Met Ala Asp
    290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
            340                 345                 350

Gln Thr Ser Tyr Val Phe Leu Gly Ile Val Leu Ala Leu Ile Gly Ala
        355                 360                 365

Ile Phe Leu Leu Val Leu Tyr Leu Asn Arg Lys Gly Ile Lys Lys Trp
    370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
                405                 410                 415

Asn Ser Asp Val
            420

<210> SEQ ID NO 12
<211> LENGTH: 446
<212> TYPE: PRT
<213> ORGANISM: Artificial Sequence
<220> FEATURE:
<223> OTHER INFORMATION: Synthetic Sequence Humanized A1 human IgG4m
      heavy chain

<400> SEQUENCE: 12
```

```
Glu Val Gln Leu Val Glu Ser Gly Gly Gly Leu Val Gln Pro Gly Gly
  1               5                   10                  15

Ser Leu Arg Leu Ser Cys Ala Ala Ser Gly Tyr Thr Phe Thr Asn Phe
             20                  25                  30

Gly Met Asn Trp Val Arg Gln Ala Pro Gly Lys Gly Leu Glu Trp Val
         35                  40                  45

Ala Trp Ile Asn Thr Asn Thr Gly Glu Pro Arg Tyr Ala Glu Glu Phe
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Trp Asp Gly Ala Tyr Phe Phe Asp Tyr Trp Gly Gln Gly
             100                 105                 110

Thr Leu Val Thr Val Ser Ser Ala Ser Thr Lys Gly Pro Ser Val Phe
             115                 120                 125

Pro Leu Ala Pro Cys Ser Arg Ser Thr Ser Glu Ser Thr Ala Ala Leu
 130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Lys Thr Tyr Thr Cys Asn Val Asp His Lys Pro
             195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                 245                 250                 255

Glu Val Thr Cys Val Val Val Asp Val Ser Gln Glu Asp Pro Glu Val
             260                 265                 270

Gln Phe Asn Trp Tyr Val Asp Gly Val Glu Val His Asn Ala Lys Thr
         275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                 325                 330                 335

Lys Ala Lys Gly Gln Pro Arg Glu Pro Gln Val Tyr Thr Leu Pro Pro
             340                 345                 350

Ser Gln Glu Glu Met Thr Lys Asn Gln Val Ser Leu Thr Cys Leu Val
             355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                 405                 410                 415

Gln Glu Gly Asn Val Phe Ser Cys Ser Val Met His Glu Ala Leu His
```

```
                    420                 425                 430
Asn His Tyr Thr Gln Lys Ser Leu Ser Leu Ser Leu Gly Lys
        435                 440                 445

<210> SEQ ID NO 13
<211> LENGTH: 119
<212> TYPE: PRT
<213> ORGANISM: Artificial Sequence
<220> FEATURE:
<223> OTHER INFORMATION: Synthetic Sequence human IgG4m VH (A1-IGG4-VH)

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Phe
            20                  25                  30

Gly Met Asn Trp Val Arg Gln Ala Pro Gly Lys Gly Leu Glu Trp Val
        35                  40                  45

Ala Trp Ile Asn Thr Asn Thr Gly Glu Pro Arg Tyr Ala Glu Glu Phe
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Asp Gly Ala Tyr Phe Phe Asp Tyr Trp Gly Gln Gly
            100                 105                 110

Thr Leu Val Thr Val Ser Ser
        115

<210> SEQ ID NO 14
<211> LENGTH: 5
<212> TYPE: PRT
<213> ORGANISM: Artificial Sequence
<220> FEATURE:
<223> OTHER INFORMATION: Synthetic Sequence A1-IgG4-VH-CDR1

<400> SEQUENCE: 14

Asn Phe Gly Met Asn
1               5

<210> SEQ ID NO 15
<211> LENGTH: 452
<212> TYPE: PRT
<213> ORGANISM: Artificial Sequence
<220> FEATURE:
<223> OTHER INFORMATION: Synthetic Sequence Chimeric A3 heavy chain
      (muA3-huIgG1)

<400> SEQUENCE: 15

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95
```

```
Tyr Cys Val Arg Gln Trp Asp Tyr Asp Val Arg Ala Met Asn Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 16
<211> LENGTH: 122
<212> TYPE: PRT
<213> ORGANISM: Artificial Sequence
<220> FEATURE:
<223> OTHER INFORMATION: Synthetic Sequence Chimeric A3 VH

<400> SEQUENCE: 16
```

```
Glu Val Gln Leu Val Glu Ser Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gln Trp Asp Tyr Asp Val Arg Ala Met Asn Tyr Trp
            100                 105                 110

Gly Gln Gly Thr Leu Val Thr Val Ser Ser
            115                 120

<210> SEQ ID NO 17
<211> LENGTH: 5
<212> TYPE: PRT
<213> ORGANISM: Artificial Sequence
<220> FEATURE:
<223> OTHER INFORMATION: Synthetic Sequence Chimeric A3 VH-CDR1

<400> SEQUENCE: 17

Thr Tyr Ala Met Asn
1               5

<210> SEQ ID NO 18
<211> LENGTH: 19
<212> TYPE: PRT
<213> ORGANISM: Artificial Sequence
<220> FEATURE:
<223> OTHER INFORMATION: Synthetic Sequence Chimeric A3 VH-CDR2

<400> SEQUENCE: 18

Arg Ile Arg Ser Lys Ser Asn Asn Tyr Ala Thr Tyr Tyr Ala Asp Ser
1               5                   10                  15

Val Lys Asp

<210> SEQ ID NO 19
<211> LENGTH: 11
<212> TYPE: PRT
<213> ORGANISM: Artificial Sequence
<220> FEATURE:
<223> OTHER INFORMATION: Synthetic Sequence Chimeric A3 VH-CDR3

<400> SEQUENCE: 19

Gln Trp Asp Tyr Asp Val Arg Ala Met Asn Tyr
1               5                   10

<210> SEQ ID NO 20
<211> LENGTH: 214
<212> TYPE: PRT
<213> ORGANISM: Artificial Sequence
<220> FEATURE:
<223> OTHER INFORMATION: Synthetic Sequence Chimeric A3 light chain
      (muA3-huKappa)

<400> SEQUENCE: 20

Asp Ile Val Met Thr Gln Ser His Ile Phe Met Ser Thr Ser Val Gly
1               5                   10                  15

Asp Arg Val Ser Ile Thr Cys Lys Ala Ser Gln Asp Val Asp Thr Ala
```

```
                        20                  25                  30
Val Ala Trp Tyr Gln Gln Lys Pro Gly Gln Ser Pro Lys Leu Leu Ile
            35                  40                  45

Tyr Trp Ala Ser Thr Arg Leu Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 107
<212> TYPE: PRT
<213> ORGANISM: Artificial Sequence
<220> FEATURE:
<223> OTHER INFORMATION: Synthetic Sequence Chimeric A3 VL

<400> SEQUENCE: 21

Asp Ile Val Met Thr Gln Ser His Ile Phe Met Ser Thr Ser Val Gly
1               5                   10                  15

Asp Arg Val Ser Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
            35                  40                  45

Tyr Trp Ala Ser Thr Arg Leu Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gln Gly Thr Lys Leu Glu Ile Lys
            100                 105

<210> SEQ ID NO 22
<211> LENGTH: 11
<212> TYPE: PRT
<213> ORGANISM: Artificial Sequence
<220> FEATURE:
<223> OTHER INFORMATION: Synthetic Sequence Chimeric A3 VL-CDR1

<400> SEQUENCE: 22

Lys Ala Ser Gln Asp Val Asp Thr Ala Val Ala
```

```
1               5                   10
```

<210> SEQ ID NO 23
<211> LENGTH: 7
<212> TYPE: PRT
<213> ORGANISM: Artificial Sequence
<220> FEATURE:
<223> OTHER INFORMATION: Synthetic Sequence Chimeric A3 VL-CDR2

<400> SEQUENCE: 23

Trp Ala Ser Thr Arg Leu Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Sequence Chimeric A3 VL-CDR3

<400> SEQUENCE: 24

Gln Gln Tyr Ser Ser Tyr Pro Tyr Thr
1               5

<210> SEQ ID NO 25
<211> LENGTH: 452
<212> TYPE: PRT
<213> ORGANISM: Artificial Sequence
<220> FEATURE:
<223> OTHER INFORMATION: Synthetic Sequence Humanized A3 human IgG1
      heavy chain

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg Gln Trp Asp Tyr Asp Val Arg Ala Met Asn Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

```
Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 26
<211> LENGTH: 122
<212> TYPE: PRT
<213> ORGANISM: Artificial Sequence
<220> FEATURE:
<223> OTHER INFORMATION: Synthetic Sequence Humanized A3 VH

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg Gln Trp Asp Tyr Asp Val Arg Ala Met Asn Tyr Trp
            100                 105                 110

Gly Gln Gly Thr Leu Val Thr Val Ser Ser
        115                 120
```

<210> SEQ ID NO 27
<211> LENGTH: 5
<212> TYPE: PRT
<213> ORGANISM: Artificial Sequence
<220> FEATURE:
<223> OTHER INFORMATION: Synthetic Sequence Humanized A3 VH-CDR1

<400> SEQUENCE: 27

Thr Tyr Ala Met Asn
1               5

<210> SEQ ID NO 28
<211> LENGTH: 19
<212> TYPE: PRT
<213> ORGANISM: Artificial Sequence
<220> FEATURE:
<223> OTHER INFORMATION: Synthetic Sequence Humanized A3 VH-CDR2

<400> SEQUENCE: 28

Arg Ile Arg Ser Lys Ser Asn Asn Tyr Ala Thr Tyr Tyr Ala Asp Ser
1               5                   10                  15

Val Lys Asp

<210> SEQ ID NO 29
<211> LENGTH: 11
<212> TYPE: PRT
<213> ORGANISM: Artificial Sequence
<220> FEATURE:
<223> OTHER INFORMATION: Synthetic Sequence Humanized A3 VH-CDR3

<400> SEQUENCE: 29

Gln Trp Asp Tyr Asp Val Arg Ala Met Asn Tyr
1               5                   10

<210> SEQ ID NO 30
<211> LENGTH: 214
<212> TYPE: PRT
<213> ORGANISM: Artificial Sequence
<220> FEATURE:
<223> OTHER INFORMATION: Synthetic Sequence Humanized A3 human Kappa
      light chain

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asp Thr Ala
                20                  25                  30

Val Ala Trp Tyr Gln Gln Lys Pro Gly Lys Ala Pro Lys Leu Leu Ile
            35                  40                  45

Tyr Trp Ala Ser Thr Arg Leu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 107
<212> TYPE: PRT
<213> ORGANISM: Artificial Sequence
<220> FEATURE:
<223> OTHER INFORMATION: Synthetic Sequence Humanized A3 VL

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg Leu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Tyr
                85                  90                  95

Thr Phe Gly Gln Gly Thr Lys Leu Glu Ile Lys
            100                 105

<210> SEQ ID NO 32
<211> LENGTH: 11
<212> TYPE: PRT
<213> ORGANISM: Artificial Sequence
<220> FEATURE:
<223> OTHER INFORMATION: Synthetic Sequence Humanized A3 VL-CDR1

<400> SEQUENCE: 32

Lys Ala Ser Gln Asp Val Asp Thr Ala Val Ala
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Synthetic Sequence Humanized A3 VL-CDR2

<400> SEQUENCE: 33

Trp Ala Ser Thr Arg Leu Thr
1               5

<210> SEQ ID NO 34
<211> LENGTH: 9
<212> TYPE: PRT
<213> ORGANISM: Artificial Sequence
```

```
<220> FEATURE:
<223> OTHER INFORMATION: Synthetic Sequence Humanized A3 VL-CDR3

<400> SEQUENCE: 34

Gln Gln Tyr Ser Ser Tyr Pro Tyr Thr
1               5
```